(12) United States Patent
Okada et al.

(10) Patent No.: US 10,408,766 B2
(45) Date of Patent: Sep. 10, 2019

(54) INSPECTION DEVICE AND INSPECTION SYSTEM

(71) Applicant: Bosch Packaging Technology K.K., Tokyo (JP)

(72) Inventors: Takao Okada, Tokyo (JP); Kosuke Takeshita, Tokyo (JP); Takashi Tanaka, Tokyo (JP)

(73) Assignee: Bosch Packaging Technology K.K., Tokyo (JP)

( * ) Notice: Subject to any disclaimer, the term of this patent is extended or adjusted under 35 U.S.C. 154(b) by 0 days.

(21) Appl. No.: 15/547,617

(22) PCT Filed: Jan. 26, 2016

(86) PCT No.: PCT/JP2016/052170
§ 371 (c)(1),
(2) Date: Jul. 31, 2017

(87) PCT Pub. No.: WO2016/125633
PCT Pub. Date: Aug. 11, 2016

(65) Prior Publication Data
US 2018/0031490 A1   Feb. 1, 2018

(30) Foreign Application Priority Data

Feb. 4, 2015   (JP) .................................. 2015-020038

(51) Int. Cl.
*G01N 21/88*   (2006.01)
*G01N 21/892*   (2006.01)
(Continued)

(52) U.S. Cl.
CPC ......... *G01N 21/8806* (2013.01); *G01N 21/21* (2013.01); *G01N 21/8851* (2013.01);
(Continued)

(58) Field of Classification Search
CPC ............... G01N 21/8806; G01N 21/21; G01N 21/8851; G01N 21/892; G01N 2021/8848; G01N 2021/8822; G06T 7/0002

See application file for complete search history.

(56) References Cited

U.S. PATENT DOCUMENTS

| 4,673,973 A | 6/1987 | Ledley |
| 4,912,318 A * | 3/1990 | Kajiura .................. B07C 5/126 209/526 |

(Continued)

FOREIGN PATENT DOCUMENTS

| CN | 1793860 A | 6/2006 |
| CN | 202548423 U | 11/2012 |

(Continued)

OTHER PUBLICATIONS

International Search Report for Application No. PCT/JP2016/052170 dated Mar. 15, 2016 (English Translation, 1 page).

*Primary Examiner* — Sang H Nguyen
(74) *Attorney, Agent, or Firm* — Michael Best & Friedrich LLP

(57) ABSTRACT

An inspection device includes an illumination unit for illuminating a subject having a bright part and a dark part darker than the bright part, a light path dividing unit for dividing object light from the subject illuminated by the illumination unit into first light and second light that pass through different light paths, a filter for reducing the amount of the first light having passed through the light path dividing unit, a first imaging unit in which the first light having passed through the filter forms an image, a second imaging unit in which the second light having passed through the light path dividing unit forms an image, and an inspection unit for inspecting whether a defect is present in (Continued)

the subject based on information of the bright part taken by the first imaging unit and information of the dark part taken by the second imaging unit.

8 Claims, 10 Drawing Sheets

(51) Int. Cl.
*G06T 7/00* (2017.01)
*G01N 21/21* (2006.01)
*G01N 21/90* (2006.01)

(52) U.S. Cl.
CPC ............ *G01N 21/892* (2013.01); *G01N 21/90* (2013.01); *G01N 21/909* (2013.01); *G06T 7/0002* (2013.01); *G01N 2021/8822* (2013.01); *G01N 2021/8848* (2013.01)

(56) References Cited

U.S. PATENT DOCUMENTS

| | | | | |
|---|---|---|---|---|
| 4,943,713 | A * | 7/1990 | Yoshida | B08B 9/46 250/223 B |
| 5,051,825 | A | 9/1991 | Cochran et al. | |
| 5,466,927 | A * | 11/1995 | Kohler | G01N 21/9009 209/526 |
| 5,982,493 | A * | 11/1999 | Lehnen | G01J 3/36 250/559.23 |
| 6,198,529 | B1 * | 3/2001 | Clark, Jr. | G01N 21/95684 356/237.5 |
| 6,633,375 | B1 * | 10/2003 | Veith | G01N 21/9501 250/559.41 |
| 6,882,417 | B2 | 4/2005 | Goldberg et al. | |
| 2002/0054291 | A1 * | 5/2002 | Tsai | G01N 21/8806 356/394 |
| 2003/0179369 | A1 * | 9/2003 | Feldman | G01N 21/8806 356/237.2 |
| 2004/0000652 | A1 * | 1/2004 | Guha | G01N 21/8901 250/559.45 |
| 2004/0146295 | A1 * | 7/2004 | Furman | G01N 21/8806 398/9 |
| 2005/0174571 | A1 | 8/2005 | Cochran et al. | |
| 2006/0007434 | A1 * | 1/2006 | Furman | G01N 21/9501 356/237.2 |
| 2007/0013901 | A1 * | 1/2007 | Kim | G01N 21/9501 356/237.2 |
| 2007/0058164 | A1 * | 3/2007 | Shibata | G01N 21/95607 356/237.2 |
| 2007/0236696 | A1 * | 10/2007 | Nojima | G01N 21/9506 356/426 |
| 2008/0231846 | A1 * | 9/2008 | Ogawa | G02B 7/32 356/237.5 |
| 2009/0059215 | A1 * | 3/2009 | Mehanian | G01N 21/8806 356/237.2 |
| 2010/0295938 | A1 * | 11/2010 | Hahn | G01N 21/9501 348/126 |
| 2012/0314213 | A1 | 12/2012 | Herrmann et al. | |
| 2012/0318775 | A1 * | 12/2012 | Schwarz | B23K 26/032 219/121.63 |
| 2014/0210983 | A1 * | 7/2014 | Shimura | G02B 21/0016 348/80 |
| 2015/0316488 | A1 * | 11/2015 | Masumura | G01N 21/8806 356/237.2 |

FOREIGN PATENT DOCUMENTS

| | | |
|---|---|---|
| DE | 102006034432 A1 | 1/2008 |
| JP | H01141342 A | 6/1989 |
| JP | H0682216 A | 3/1994 |
| JP | 07298276 | 11/1995 |
| JP | 2005083877 | 3/2005 |
| JP | 2012202767 | 10/2012 |

* cited by examiner

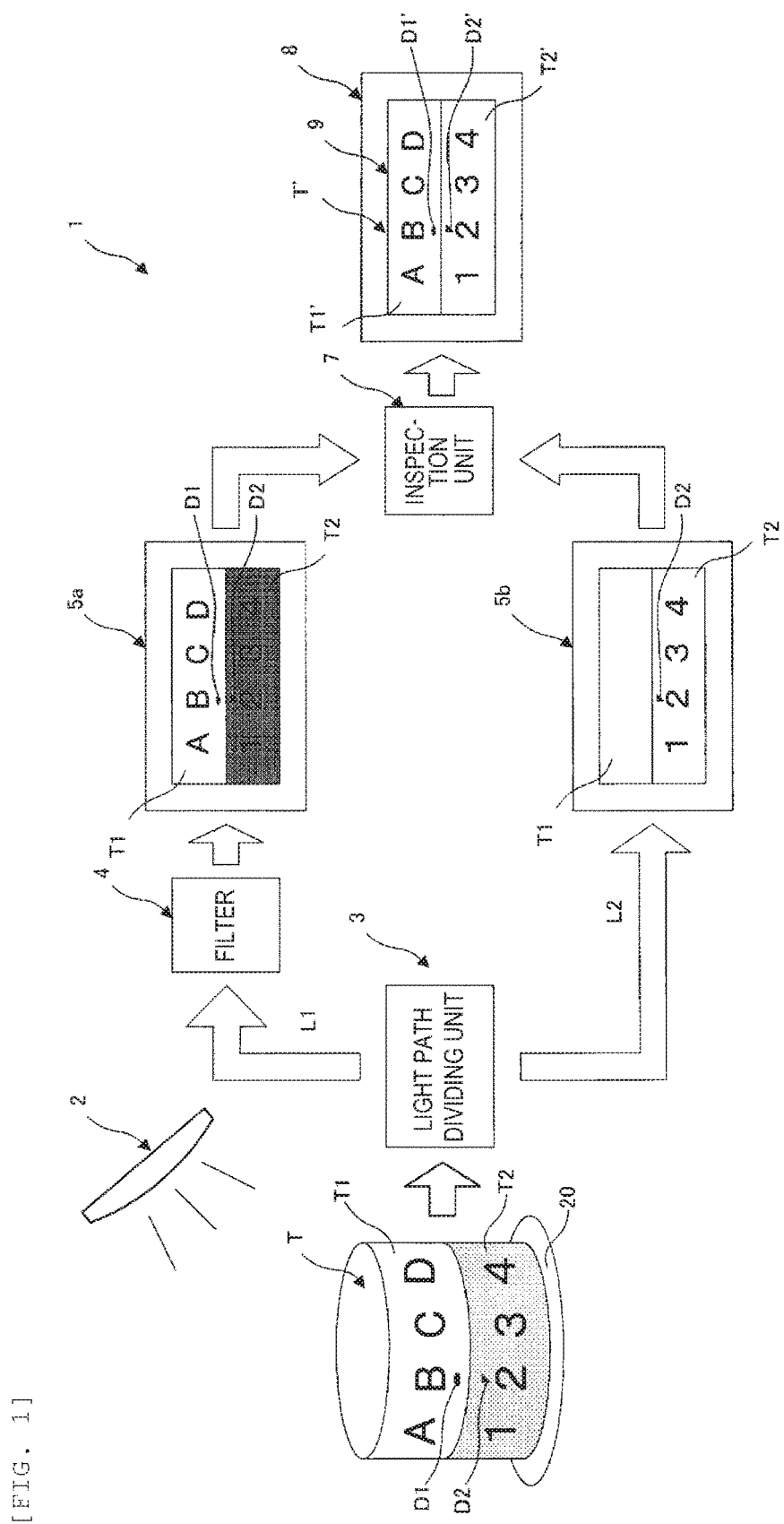
[FIG. 1]

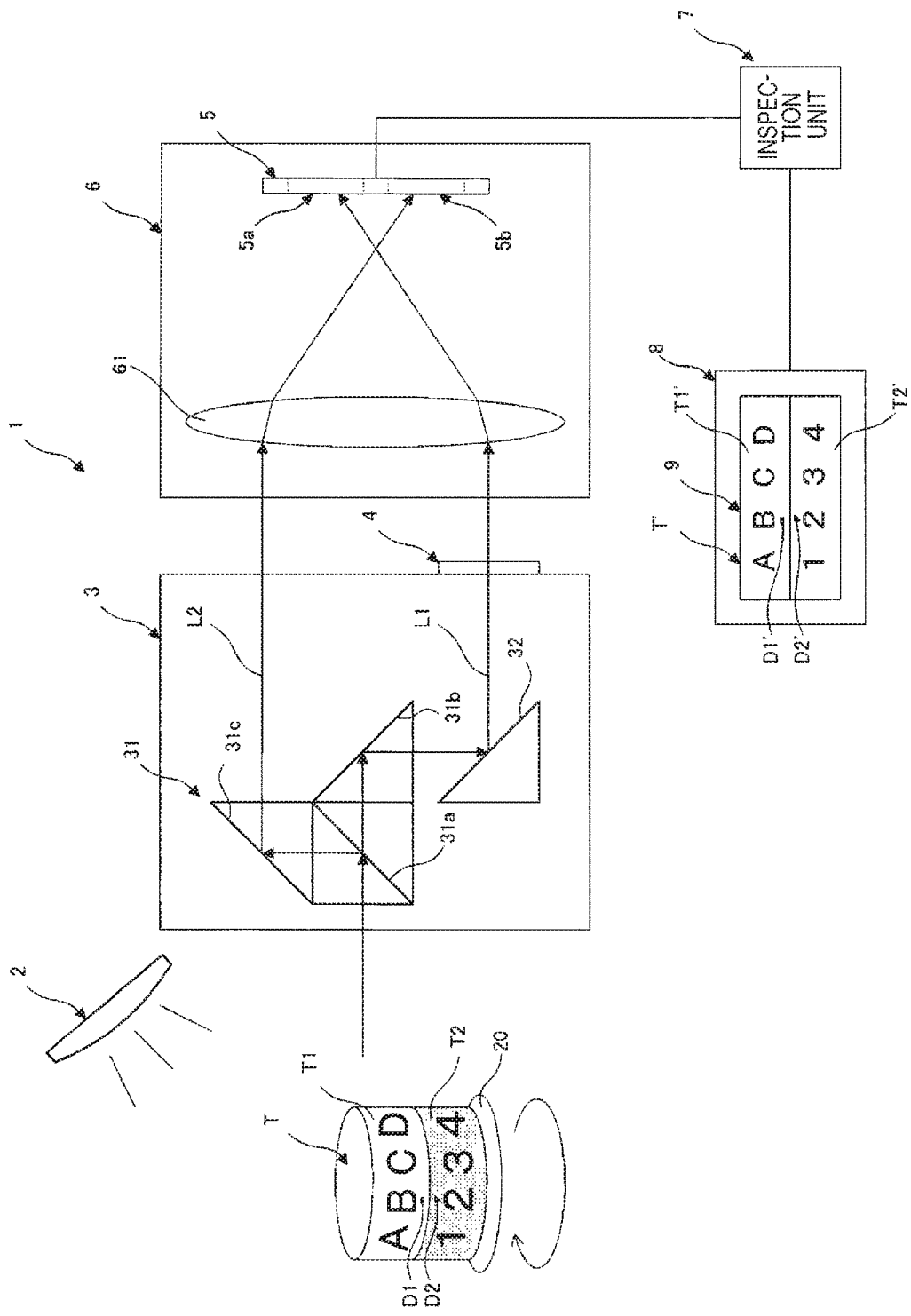

[FIG. 3]
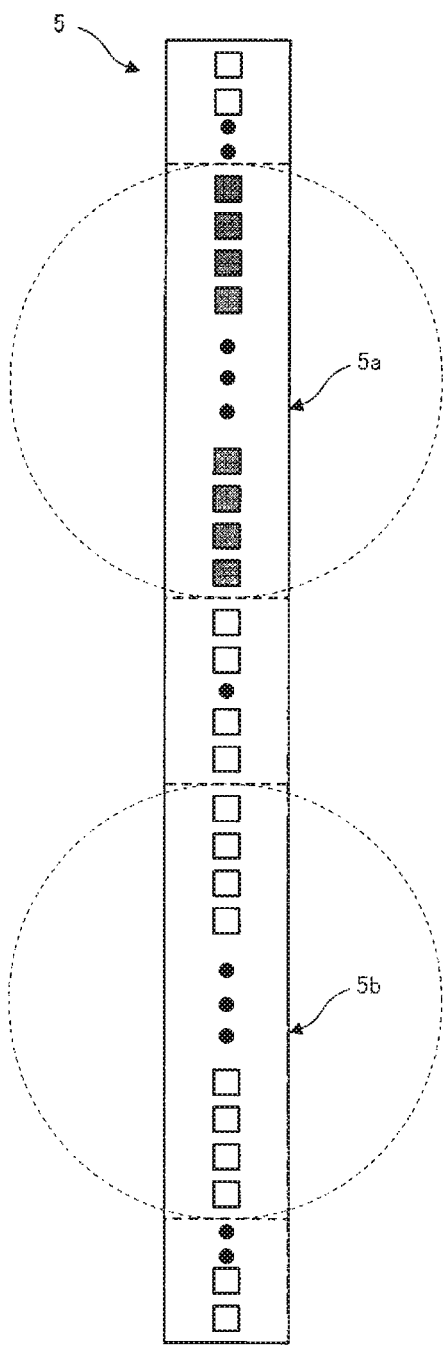

[FIG. 4]
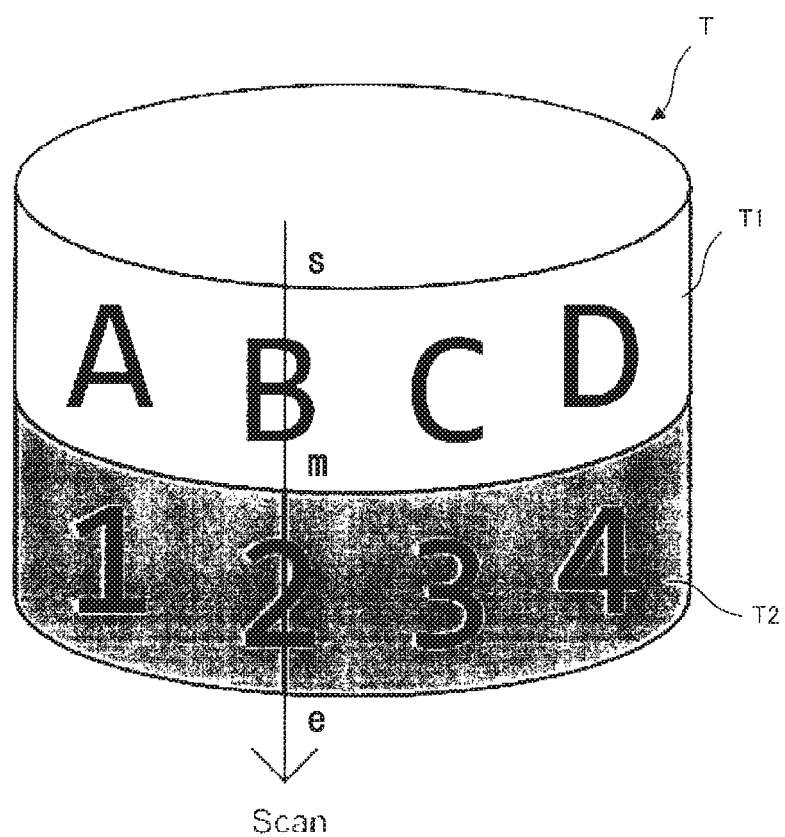

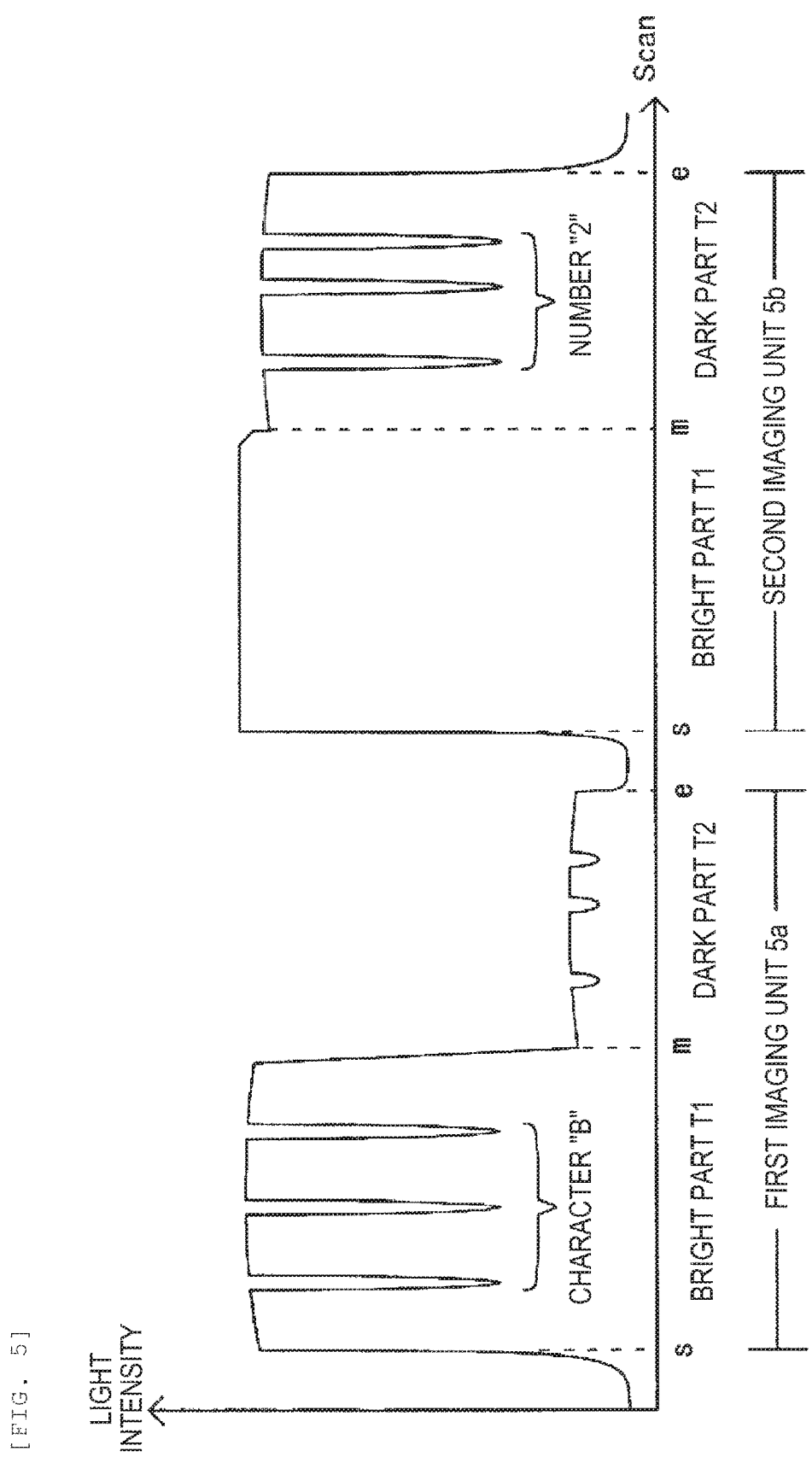

[FIG. 6]
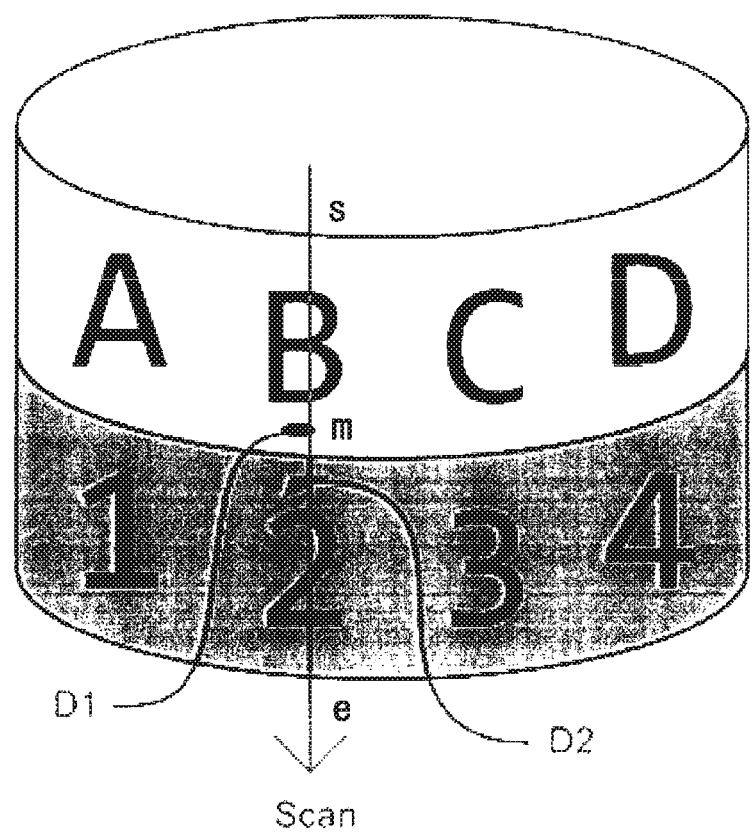

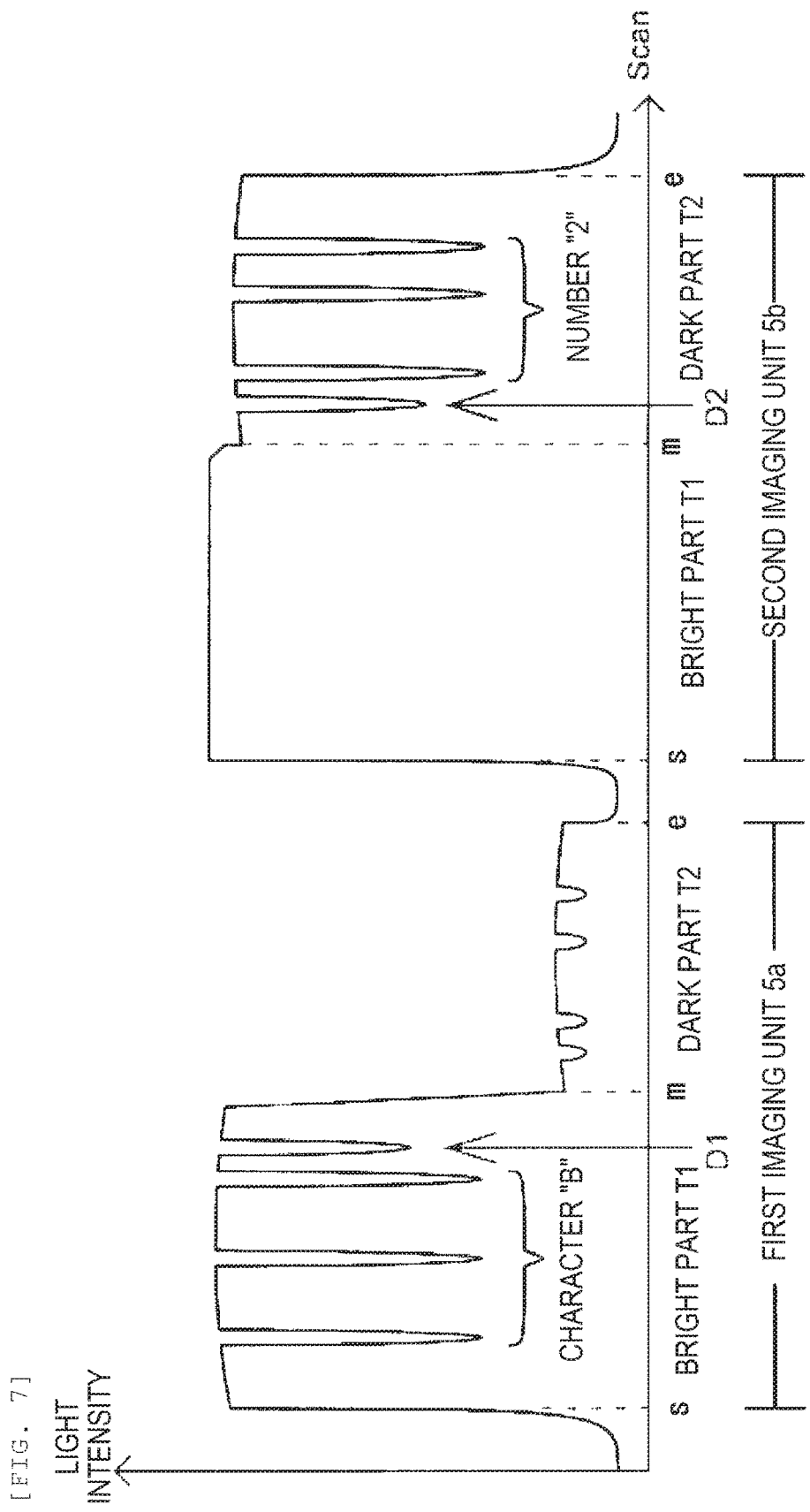

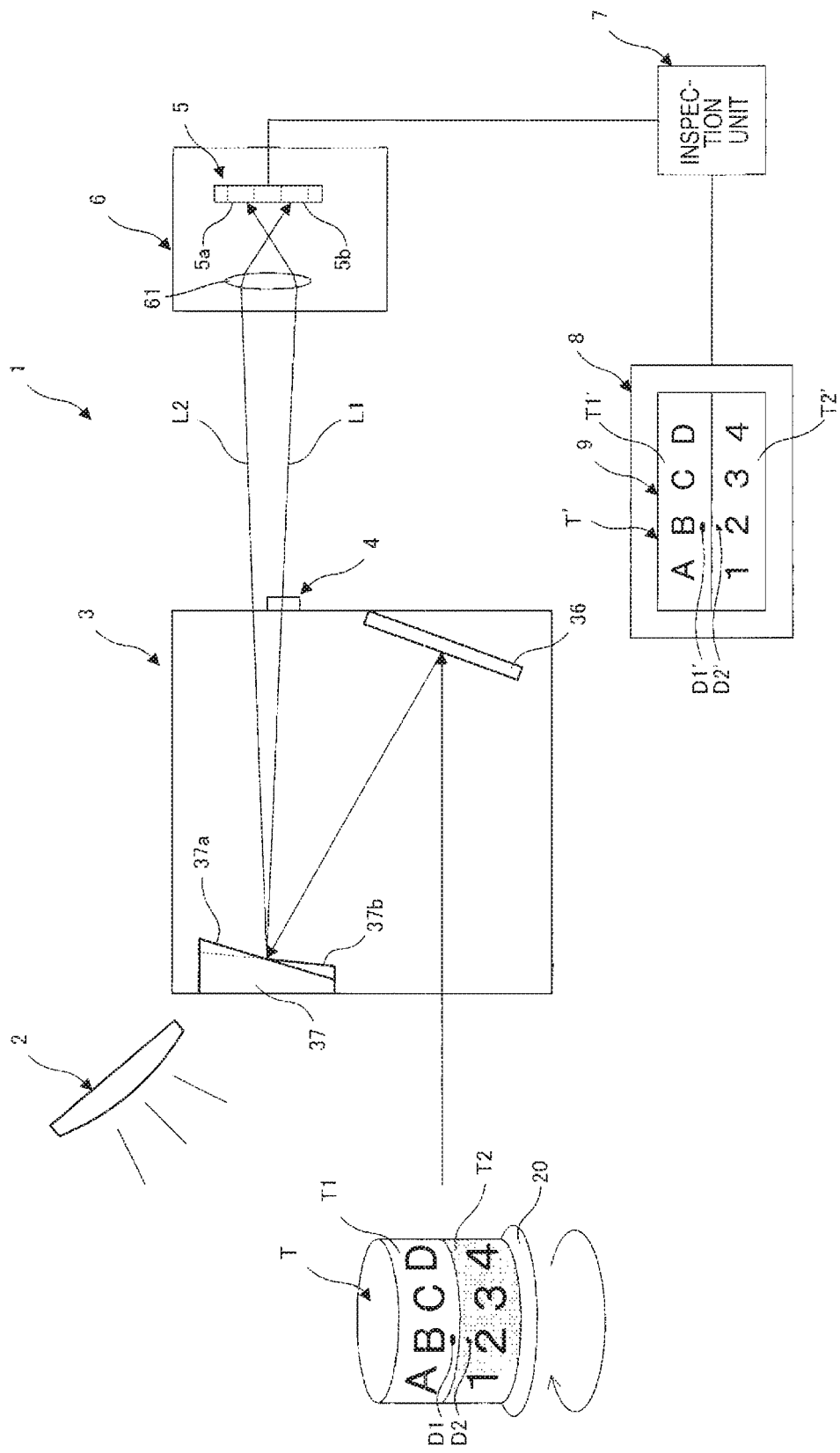
[FIG. 8]

[FIG. 9]
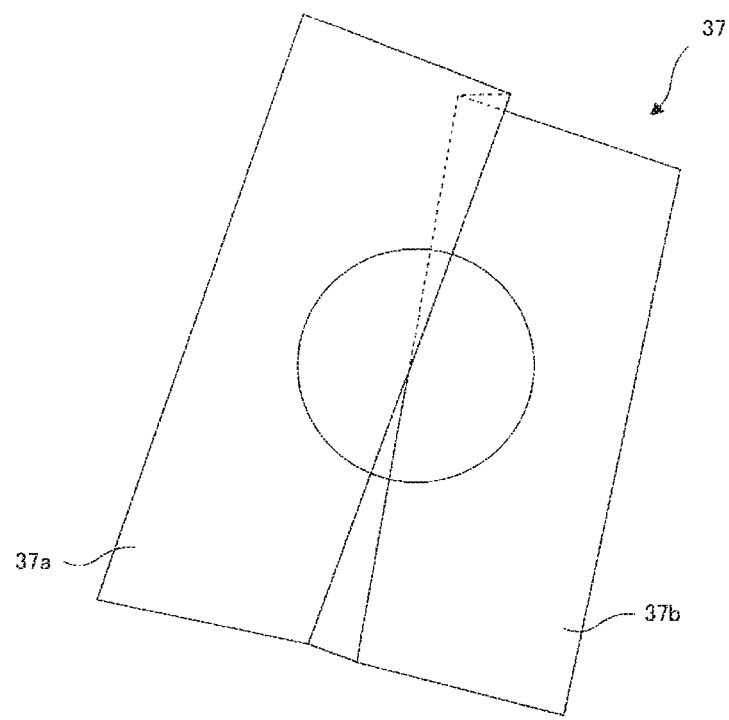
[FIG. 10]
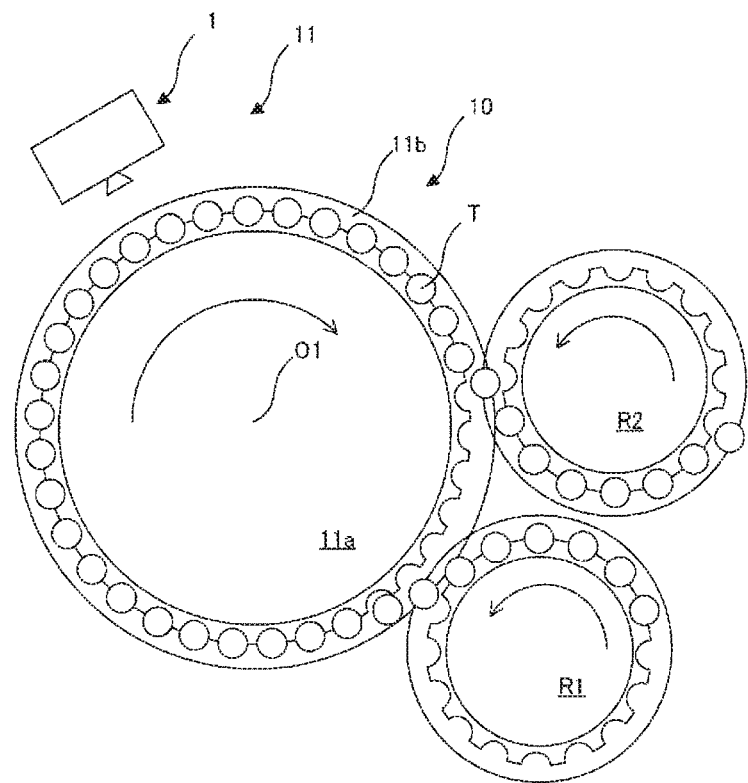

[FIG. 11]
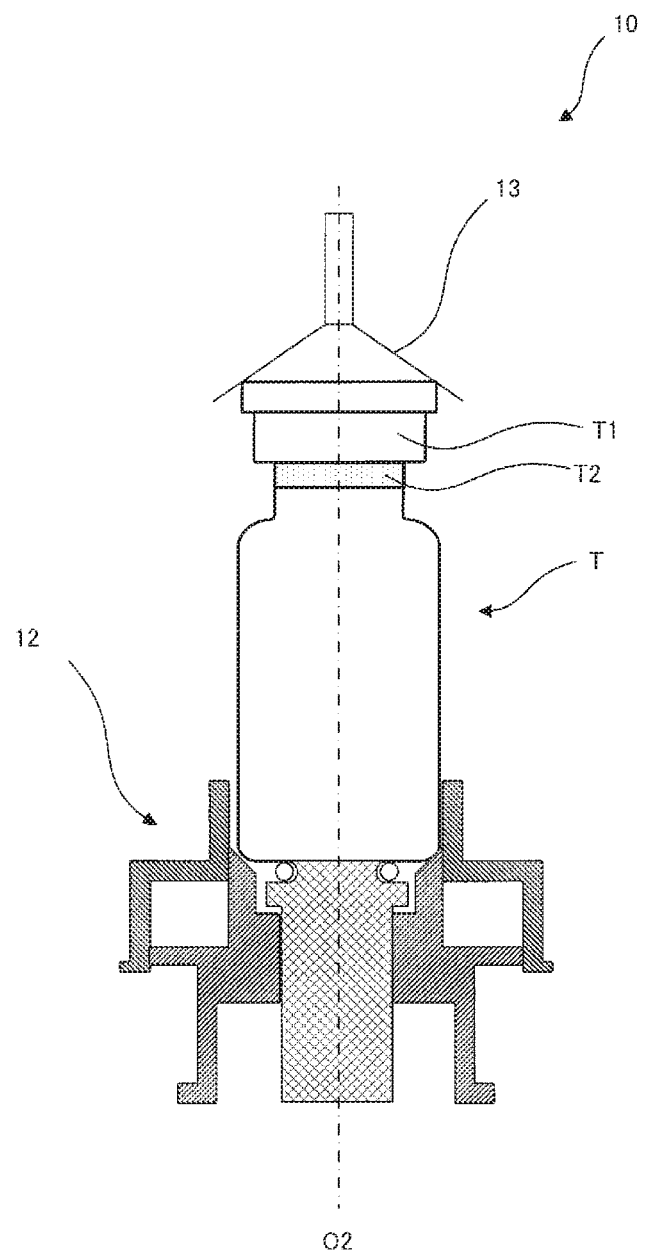

INSPECTION DEVICE AND INSPECTION SYSTEM

BACKGROUND OF THE INVENTION

The present invention relates to the technical field of an inspection device and an inspection system for inspecting defects such as flaws and soils in a subject.

Conventionally, there is disclosed an inspection device capable of inspecting different inspection items using one inspection rotor as a device for inspection and the like of containers (see JP-A-2012-202767).

SUMMARY OF THE INVENTION

However, since different inspection devices have been used for different inspection items, a plurality of inspection devices and the space for the plurality of inspection devices are necessary, thereby increasing the cost of the devices.

The invention addresses the above problems with an object of providing an inspection device and an inspection system capable of inspecting parts including variations in brightness at a time using a simple structure.

An inspection device according to the invention includes an illumination unit for illuminating a subject having a bright part and a dark part darker than the bright part, a light path dividing unit for dividing object light from the subject illuminated by the illumination unit into first light and second light that pass through different light paths, a filter for reducing the amount of the first light having passed through the light path dividing unit, a first imaging unit in which the first light having passed through the filter forms an image, a second imaging unit in which the second light having passed through the light path dividing unit forms an image, and an inspection unit for inspecting whether a defect is present in the subject based on information of the bright part imaged by the first imaging unit and information of the dark part imaged by the second imaging unit.

In addition, the inspection device according to the invention further includes a holding unit on which the subject is rotatably placed, in which each of the first imaging unit and the second imaging unit includes a plurality of optoelectronic conversion devices disposed linearly.

In addition, the light path dividing unit of the inspection device according to the invention has a prism including a beam splitter.

In addition, the light path dividing unit of the inspection device according to the invention has a reflection member including a first reflection surface and a second reflection surface adjacent to each other, the first reflection surface and the second reflection surface being inclined at angles different from each other.

In addition, the inspection device according to the invention further includes an image processing unit for combining an image of the bright part taken by the first imaging unit with an image of the dark part taken by the second imaging unit and a display unit for displaying an image processed by the image processing unit.

In addition, an inspection system according to the invention includes a substantially discoid rotor body rotatable about a shaft, a table rotatably supporting the subject by an outer rim of the rotor body, a cap pressing the subject from above, and the inspection device for inspecting the subject placed on the table.

An inspection device according to the invention includes an illumination unit for illuminating a subject having a bright part and a dark part darker than the bright part, a light path dividing unit for dividing object light from the subject illuminated by the illumination unit into first light and second light that pass through different light paths, a filter for reducing the amount of the first light having passed through the light path dividing unit, a first imaging unit in which the first light having passed through the filter forms an image, a second imaging unit in which the second light having passed through the light path dividing unit forms an image, and an inspection unit for inspecting whether a defect is present in the subject based on information of the bright part imaged by the first imaging unit and information of the dark part imaged by the second imaging unit. Accordingly, parts including variations in brightness can be inspected at a time using a simple structure.

In addition, the inspection device according to the invention further includes a holding unit on which the subject is rotatably placed, in which each of the first imaging unit and the second imaging unit includes a plurality of optoelectronic conversion devices disposed linearly. Accordingly, a high-resolution image can be displayed.

In addition, the light path dividing unit of the inspection device according to the invention has a prism including a beam splitter. Accordingly, a light path can be divided using a simple structure.

In addition, the light path dividing unit of the inspection device according to the invention has a reflection member including a first reflection surface and a second reflection surface adjacent to each other, the first reflection surface and the second reflection surface being inclined at angles different from each other. Accordingly, a light path can be divided using a simple structure.

In addition, the inspection device according to the invention further includes an image processing unit for combining an image of the bright part taken by the first imaging unit with an image of the dark part taken by the second imaging unit and a display unit for displaying an image processed by the image processing unit. Accordingly, defects in the bright part and defects in the dark part can be observed on one screen of the display unit.

In addition, an inspection system according to the invention includes a substantially discoid rotor body rotatable about a shaft, a table rotatably supporting the subject by an outer rim of the rotor body, a cap pressing the subject from above, and the inspection device for inspecting the subject placed on the table. Accordingly, parts including variations in brightness can be inspected at a time using a simple structure.

BRIEF DESCRIPTION OF THE DRAWINGS

FIG. 1 is a conceptual diagram illustrating an inspection device according to the invention.

FIG. 2 illustrates an inspection device according to a first embodiment of the invention.

FIG. 3 illustrates imaging units of the inspection device according to the first embodiment of the invention.

FIG. 4 illustrates the scan method of the imaging units of the inspection device according to the first embodiment of the invention.

FIG. 5 illustrates the intensity of light obtained by the inspection unit of the inspection device according to the first embodiment of the invention when no defects are present.

FIG. 6 illustrates how the imaging units of the inspection device according to the first embodiment of the invention scan defective portions in a subject.

FIG. 7 illustrates the intensity of light obtained by the inspection unit of the inspection device according to the first embodiment of the invention when defects are present in the subject.

FIG. 8 illustrates an inspection device according to a second embodiment of the invention.

FIG. 9 is a perspective view illustrating a reflection member of the inspection device according to the second embodiment of the invention.

FIG. 10 is a conceptual diagram of an inspection system according to the invention.

FIG. 11 is a conceptual diagram of the subject inspected by the inspection system according to the invention.

DETAILED DESCRIPTION

Embodiments of the invention will be described below with reference to the drawings.

FIG. 1 is a conceptual diagram illustrating an inspection device 1 according to the embodiment.

The inspection device 1 according to the embodiment includes an illumination unit 2 for illuminating a subject T having a bright part T1 and a dark part T2, a light path dividing unit 3 for dividing the light path of object light from the subject T illuminated by the illumination unit 2, a filter 4 for reducing the amount of a first light L1 having passed through the light path dividing unit 3, a first imaging unit 5a in which the light having passed through the filter 4 forms an image, a second imaging unit 5b in which a second light L2 having passed through the light path dividing unit 3 forms an image, and an inspection unit 7 for inspecting whether a defect is present based on information of the bright part taken by the first imaging unit 5a and information of the dark part taken by the second imaging unit 5b, an image processing unit 8 for combining an image of the bright part taken by the first imaging unit 5a with an image of the dark part taken by the second imaging unit 5b, and a display unit 9 for displaying an image processed by the image processing unit 8.

The illumination unit 2 illuminates the subject T with high-intensity light. The subject T in the embodiment has the bright part T1 made of metal or the like and the dark part T2 made of rubber or the like. The light with which the subject T is illuminated by the illumination unit 2 enters the light path dividing unit 3 as object light.

The light path dividing unit 3 divides the light path of object light using a beam splitter or the like. One of the divided light beams passes through the filter 4 as the first light L1. The filter 4 reduces the amount of light without having effects on the color using an ND (Neutral Density) filter or the like. The first light L1 that has passed through the filter 4 and the amount of light thereof is reduced forms an image in the first imaging unit 5a of the linear imaging device (such as a CCD) 5. The other of the divided light beams forms an image in the second imaging unit 5b, which is another section of the imaging device 5, as the second light L2. Since the second light L2 does not pass through the filter 4 or the like, the amount of light thereof is not reduced. It should be noted that the second light L2 may pass through a filter (not illustrated) that reduces a less amount of light than the filter 4 through which the first light L1 has passed through.

Since the amount of light of the image formed in the first imaging unit 5a has been reduced, the image of the bright part T1 of the subject T can be inspected, but the image of the dark part T2 is too dark and cannot be inspected. In addition, since the amount of light does not change due to the filter or the like in the image formed in the second imaging unit 5b, the image of the bright part T1 of the subject T is too bright and cannot be inspected, but the image of the dark part T2 can be inspected.

The inspection unit 7 inspects whether defects are present based on information of the bright part T1 taken by the first imaging unit 5a and information of the dark part T2 taken by the second imaging unit 5b. The inspection method will be described later.

The image processing unit 8 combines an image T1' of the bright part T1 taken by the first imaging unit 5a with an image T2' of the dark part T2 taken by the second imaging unit 5b. The display unit 9 displays an image T' combined by the image processing unit 8. As illustrated in FIG. 1, the bright part T1 and the dark part T2 of the subject T can be observed on one screen in the combined image T'. For example, as illustrated in FIG. 1, a defect D1 in the bright part T1 and a defect D2 in the dark part T2 can be observed as D1' and D2', respectively, on one screen.

As described above, the inspection device 1 according to the embodiment can inspect parts including variations in brightness at a time using a simple structure.

Next, the first embodiment will be described.

FIG. 2 illustrates an inspection device 1 according to the first embodiment.

The inspection device 1 according to the first embodiment includes the illumination unit 2 for illuminating the subject T having the bright part T1 and the dark part T2, the light path dividing unit 3 for dividing the light path of object light from the subject T illuminated by the illumination unit 2, the filter 4 for reducing the amount of the first light L1 having passed through the light path dividing unit 3, the first imaging unit 5a in which the light having passed through the filter 4 forms an image, the second imaging unit 5b in which the second light L2 having passed through the light path dividing unit 3 forms an image, the inspection unit 7 for inspecting whether a defect is present based on information of the bright part taken by the first imaging unit 5a and information of the dark part taken by the second imaging unit 5b, the image processing unit 8 for combining an image of the bright part taken by the first imaging unit 5a with an image of the dark part taken by the second imaging unit 5b, and the display unit 9 for displaying an image processed by the image processing unit 8. In addition, the inspection device 1 according to the first embodiment has a holding unit 20 on which the subject T is rotatably placed.

The illumination unit 2 illuminates the subject T with high-intensity light. The subject T in the embodiment has the bright part T1 made of metal or the like and the dark part T2 made of rubber or the like. The light with which the subject T is illuminated by the illumination unit 2 enters the light path dividing unit 3 as object light. The subject T in the first embodiment is placed on a stage (not illustrated) and rotates.

In the first embodiment, light is divided using a prism 31 and a reflection member 32 as the light path dividing unit 3. A beam splitter 31a is installed in the prism 31 to divide light. The beam splitter 31a can adjust the amount of light on the transmission side and the amount of light on the opposite side. For example, the amount of light transmitting through the beam splitter 31a may be set to 70% and the amount of light reflected by the beam splitter 31a may be set to 30%, for example.

The first light L1 having transmitted through the beam splitter 31a is reflected again by a first reflection surface 31b in the prism 31 and exits the prism 31. The first light L1 is further reflected by the reflection member 32, looses the amount of light thereof by passing through the filter 4, is refracted by a lens 61 built in a camera 6, and forms an image in the first imaging unit 5*a*.

The first reflection surface 31*b* and the reflection member 32 are used to make the light path lengths of the first light L1 and the second light L2 identical.

The second light L2 reflected by the beam splitter 31*a* is reflected again by a second reflection surface 31*c* in the prism, and exits the prism 31. The second light L2 is refracted by the lens 61 built in the camera 6 and forms an image in the second imaging unit 5*b*.

FIG. 3 illustrates the imaging units 5*a* and 5*b* of the inspection device 1 according to the first embodiment. FIG. 4 illustrates the scan method of the imaging unit 5*a* and 5*b* of the inspection device 1 according to the first embodiment.

The first imaging unit 5*a* and the second imaging unit 5*b* of the inspection device 1 according to the first embodiment constitute the imaging device 5 in which optoelectronic conversion devices are arranged linearly. In the first imaging unit 5*a* and the second imaging unit 5*b*, light from the subject T that is rotating forms an image linearly. For example, as illustrated in FIG. 4, scanning is performed from up to down in a straight line and the first imaging unit 5*a* and the second imaging unit 5*b* read information linearly. The brightness information on an outer circumference for one turn can be obtained by scanning the subject T for one turn in sequence.

FIG. 5 illustrates the intensity of light obtained by the inspection unit 7 of the inspection device 1 according to the first embodiment when no defects are present.

The inspection unit 7 reads information sent from the first imaging unit 5*a* and the second imaging unit 5*b* and inspects whether defects are present in the subject T. In FIG. 5, the horizontal axis represents the scan position and the vertical axis represents the intensity of light. For example, when the position corresponding to the character "B" and the number "2" is scanned in the direction indicated by s, m, and e as illustrated by an arrow in FIG. 4, the character "B" in the bright part T1 and the number "2" in the dark part T2 are partially scanned linearly.

The entire amount of first light L1 that enters the first imaging unit 5*a* is reduced because the light has passed through the filter 4. Accordingly, in the dark part T2, the intensity of the part of the number "2" and the intensity of the part not including this number are low and the difference cannot be identified easily. In contrast, in the bright part T1, the intensity of the black part of the character "B" is low and the intensity of the part not including this character is high. Accordingly, the intensity of the light is reduced when outlines of the character "B" are crossed during scanning and grooves are formed as illustrated in FIG. 5.

Since the second light L2 that enters the second imaging unit 5*b* does not pass through the filter 4, the entire amount of light is high. Accordingly, the intensity of the part of the character "B" in the bright part T1 and the intensity of the part not including this character are high, so the difference cannot be identified easily. In contrast, in the dark part T2, the intensity of the light is low in the black part of the number "2" and the intensity of the part not including this number is high. Accordingly, the intensity of the light is reduced when outlines of the number "2" are crossed during scanning and grooves are formed as illustrated in FIG. 5.

If such scanning is performed for one turn, the characters and numbers of the subject T can be identified.

FIG. 6 illustrates how the imaging units 5*a* and 5*b* of the inspection device 1 according to the first embodiment scan defective portions in the subject T. FIG. 7 illustrates the intensity of light obtained by the inspection unit 7 of the inspection device 1 according to the first embodiment when defects are present in the subject T.

It is assumed that the first defect D1 is present below the character "B" in the bright part T1 of the subject T and the second defect D2 is present above the number "2" in the dark part T2 and scanning of the corresponding positions is performed in the direction indicated by s, m, and e as illustrated by an arrow in FIG. 6.

The entire amount of first light L1 that enters the first imaging unit 5*a* is reduced because the light has passed through the filter 4. Accordingly, in the dark part T2, the intensity of the part of the number "2" and the intensity of the part not including this number are low and the difference cannot be identified easily. In contrast, in the bright part T1, the intensity of the light of the black part of the character "B" is low and the intensity of the part not including this character is high. Accordingly, the intensity of the light is reduced when outlines of the character "B" are crossed during scanning and grooves are formed as illustrated in FIG. 7. If the first defect D1 is present, a groove other than in the character "B" is formed.

Since the second light L2 that enters the second imaging unit 5*b* does not pass through the filter 4, the entire amount of light is high. Accordingly, the intensity of the part of the character "B" in the bright part T1 and the intensity of the part not including this character are high, so the difference cannot be identified easily. In contrast, in the dark part T2, the intensity of the light is low in the black part of the number "2" and the intensity of the part not including this number is high. Accordingly, the intensity of the light is reduced when outlines of the number "2" are crossed during scanning and grooves are formed as illustrated in FIG. 7. If the second defect "D2" is present, a groove other than in the number "2" is formed.

If such scanning is performed for one turn, parts of the subject T including variations in brightness can be inspected at a time to determine whether defects are present.

The image processing unit 8 combines the image T1' of the bright part T1 taken by the first imaging unit 5*a* with the image T2' of the dark part T2 taken by the second imaging unit 5*b*. The display unit 9 displays the image combined by the image processing unit 8. As illustrated in FIG. 2, the bright part T1 and the dark part T2 of the subject T can be inspected on one screen in the combined image T'=T1'+T2'. For example, as illustrated in FIG. 2, the first defect D1 in the bright part T1 and the second defect D2 in the dark part T2 can be observed as D1' and D2', respectively, on one screen.

As described above, the inspection device 1 according to the first embodiment can inspect parts including variations in brightness at a time using a simple structure.

Next, the second embodiment will be described.

FIG. 8 illustrates an inspection device 1 according to the second embodiment.

The inspection device 1 according to the second embodiment includes the illumination unit 2 for illuminating the subject T having the bright part T1 and the dark part T2, the light path dividing unit 3 for dividing the light path of object light from the subject T illuminated by the illumination unit 2, the filter 4 for reducing the amount of the first light L1 having passed through the light path dividing unit 3, the first imaging unit 5*a* in which the light having passed through the filter 4 forms an image, the second imaging unit 5*b* in which the second light L2 having passed through the light path dividing unit 3 forms an image, the inspection unit 7 for inspecting whether a defect is present based on information of the bright part taken by the first imaging unit 5*a* and information of the dark part taken by the second imaging unit 5b, the image processing unit 8 for combining an image of the bright part taken by the first imaging unit 5a with an image of the dark part taken by the second imaging unit 5b, and the display unit 9 for displaying an image processed by the image processing unit 8.

The illumination unit 2 illuminates the subject T with high-intensity light. The subject T in the embodiment has the bright part T1 made of metal or the like and the dark part T2 made of rubber or the like. The light with which the subject T is illuminated by the illumination unit 2 enters the light path dividing unit 3 as object light. The subject T in the second embodiment is placed on a stage (not illustrated) and rotates.

In the second embodiment, light is divided using a reflection mirror 36 and a reflection member 37 as the light path dividing unit 3. The reflection mirror 36 reflects object light to the reflection member 37. The reflection member 37 reflects the light reflected by reflection mirror 36 toward the image surface. That is, a Z-shaped light path is formed by the reflection mirror 36 and the reflection member 37.

FIG. 9 is a perspective view illustrating the reflection member 37 of the inspection device 1 according to the second embodiment.

The reflection member 37 has a first reflection surface 37a and a second reflection surface 37b. The first reflection surface 37a and the second reflection surface 37b are adjacent to each other and inclined at angles different from each other.

The first light L1 reflected by the first reflection surface 37a passes through the filter 4 as illustrated in FIG. 8 and forms an image in the first imaging unit 5a as illustrated in FIG. 3. The second light L2 reflected by the second reflection surface 37b forms an image in the second imaging unit 5b as illustrated in FIG. 3.

The scan method and the processing method of the inspection unit 7, the image processing unit 8, and the display unit 9 are similar to those in the first embodiment.

As described above, the inspection device 1 according to the second embodiment can inspect parts including variations in brightness at a time using a simple structure.

Next, an example of applying the inspection device 1 according to the embodiment to an inspection system 10 will be described. The subject T in this example has the crimp unit T1 as the bright part T1 made of metal such as a vial and the rubber stopper part T2 as the dark part T2 made of rubber. The inspection device 1 inspects defects such as flaws and soils on the crimp unit T1 and the rubber stopper part T2.

FIG. 10 is a plan view illustrating the inspection system 10. FIG. 11 illustrates the subject T inspected by the inspection system 10.

The inspection system 10 according to the embodiment includes a rotor unit 11, a pack 12 as the holding unit, and a cap 13. In the inspection system 10 according to the embodiment, the subject T supported by the pack 12 and the cap 13 is transferred so as to be rotatable by a rotary mechanism (not illustrated) provided in the outer rim of the rotor unit 11 and to be hoistable by a hoist mechanism (not illustrated).

The rotor unit 11 has a substantially discoid rotor body 11a rotatable about a first shaft O1 and a table 11b supporting the rotary mechanism in the outer rim of the rotor body 11a. The rotor unit 11 rotates integrally with the pack 12 and the cap 13.

The pack 12 is rotatable about a second shaft O2 via a rotary mechanism (not illustrated). The cap 13 rotatably presses the subject T from above.

Next, the operation of the inspection system 10 will be described. In the example illustrated in FIG. 10, the case in which the subject T is inspected by the inspection device 1 will be described.

As illustrated in FIG. 10, the subject T is first transferred from an introduction rotor R1 to the rotor unit 11 in the state in which the subject T is placed on the pack 12. The subject T is placed on the pack 12 and moves on the table 11b while being pressed by the cap 13 from above and being rotated.

The inspection device 1 takes pictures of the crimp unit T1 as the bright part T1 of the subject T that is rotating and the rubber stopper part T2 as the dark part T2 of the subject T. The inspection device 1 used to take pictures may be the inspection device 1 illustrated in FIGS. 2 and 8. After that, the subject T having passed by the inspection device 1 is ejected by an ejection rotor R2 as illustrated in FIG. 10.

As described above, the inspection system 10 illustrated in FIG. 10 can inspect parts including variations in brightness at a time using a simple structure.

Since, as described above, the inspection device 1 according to the embodiment includes the illumination unit 2 for illuminating the subject T having the bright part T1 and the dark part T2 darker than the bright part T1, the light path dividing unit 3 for dividing object light from the subject T illuminated by the illumination unit 2 into the first light L1 and the second light L2 that pass through different light paths, the filter 4 for reducing the amount of the first light L1 having passed through the light path dividing unit 3, the first imaging unit 5a in which the first light L1 having passed through the filter 4 forms an image, the second imaging unit 5b in which the second light L2 having passed through the light path dividing unit 3 forms an image, and the inspection unit 7 for inspecting whether a defect is present in the subject T based on information of the bright part T1 taken by the first imaging unit 5a and information of the dark part T2 taken by the second imaging unit 5b, it is possible to inspect parts including variations in brightness at a time using a simple structure.

In addition, since the inspection device 1 according to the embodiment has the holding unit 20 on which the subject T is rotatably placed and each of the first imaging unit 5a and the second imaging unit 5b includes a plurality of optoelectronic imaging devices disposed linearly, a high-resolution image can be displayed.

In addition, since the light path dividing unit 3 has the prism 31 including the beam splitter 31a in the inspection device 1 according to the first embodiment, a light path can be divided using a simple structure.

In addition, in the inspection device 1 according to the second embodiment, the light path dividing unit 3 has the reflection member 37 including the first reflection surface 37a and the second reflection surface 37b adjacent to each other, the first reflection surface 37a and the second reflection surface 37b being inclined at angles different from each other, a light path can be divided using a simple structure.

In addition, since the inspection device 1 according to the embodiment includes the image processing unit 8 for combining the image of the bright part T1 taken by the first imaging unit 5a with the image of the dark part T2 taken by the second imaging unit 5b and the display unit 9 for displaying the image processed by the image processing unit 8, the defect D1 in the bright part T1 and the defect D2 in the dark part T2 can be observed on one screen of the display unit 9.

In addition, since the inspection system 10 according to the embodiment includes the substantially discoid rotor body 11a rotatable about a shaft, the table 11b rotatably supporting the subject T by the outer rim of the rotor body 11a, the cap 13 pressing the subject T from above, and the inspection device 1 for inspecting the subject T placed on the table 11b, parts including variations in brightness can be inspected at a time using a simple structure.

Although various embodiments of the invention have been described above, the invention is not limited to only these embodiments and embodiments obtained by changing the structures of the embodiments as appropriate or combining the structures of the embodiments as appropriate are also fall within the category of the invention without departing from the scope of the invention.

REFERENCE SIGNS LIST

1: inspection device
2: illumination unit
3: light path dividing unit
4: filter
5: imaging device
5a: first imaging unit
5b: second imaging unit
6: camera
7: inspection unit
8: image processing unit
9: display unit
20: holding unit
10: transfer system
11: rotor unit
11a: rotor body
11b: table
12: pack (holding unit)
13: cap

The invention claimed is:

1. An inspection device comprising:
an illumination unit for illuminating a subject having a bright part and a dark part darker than the bright part;
a light path dividing unit for dividing light from the subject illuminated by the illumination unit into first light and second light that pass through different light paths;
a filter for reducing the intensity of the first light having passed through the light path dividing unit;
a detection unit for capturing a combined image of an image of the bright part and an image of the dark part, the detection unit including
a first imaging unit in which the first light having passed through the filter forms the image of the bright part;
a second imaging unit in which the second light having passed through the light path dividing unit forms the image of the dark part; and
an inspection unit for inspecting whether a defect is present in the subject based on the combined image, wherein defects on the bright part and the dark part of the subject are inspected.

2. The inspection device according to claim 1, further comprising:
a holding unit on which the subject is rotatably placed, wherein each of the first imaging unit and the second imaging unit includes a plurality of optoelectronic conversion devices disposed linearly.

3. The inspection device according to claim 1, wherein the light path dividing unit has a prism including a beam splitter.

4. The inspection device according to claim 1, wherein the light path dividing unit has a reflection member including a first reflection surface and a second reflection surface adjacent to each other, the first reflection surface and the second reflection surface being inclined at angles different from each other.

5. The inspection device according to claim 1, further comprising:
an image processing unit for combining the image of the bright part taken by the first imaging unit with the image of the dark part taken by the second imaging unit; and
a display unit for displaying an image processed by the image processing unit.

6. An inspection system comprising:
a substantially discoid rotor body rotatable about a shaft;
a table rotatably supporting the subject by an outer rim of the rotor body;
a cap pressing the subject from above; and
the inspection device according to claim 1 for inspecting the subject placed on the table.

7. The inspection device according to claim 1, wherein the inspection unit inspects the image from the first imaging unit to determine whether a defect is present in the bright part of the subject.

8. The inspection device according to claim 1, wherein the inspection unit inspects the image from the second imaging unit to determine whether a defect is present in the dark part of the subject.

* * * * *